(12) United States Patent
Schröder

(10) Patent No.: US 9,320,680 B2
(45) Date of Patent: Apr. 26, 2016

(54) MULTICOMPARTMENT CONTAINER

(75) Inventor: Petronella Schröder, Malmö (SE)

(73) Assignee: Gambro Lundia AB, Lund (SE)

( * ) Notice: Subject to any disclaimer, the term of this patent is extended or adjusted under 35 U.S.C. 154(b) by 1745 days.

(21) Appl. No.: 12/517,950

(22) PCT Filed: Dec. 6, 2007

(86) PCT No.: PCT/SE2007/001091
§ 371 (c)(1),
(2), (4) Date: Jun. 5, 2009

(87) PCT Pub. No.: WO2008/069731
PCT Pub. Date: Jun. 12, 2008

(65) Prior Publication Data
US 2010/0318058 A1    Dec. 16, 2010

Related U.S. Application Data

(60) Provisional application No. 60/869,012, filed on Dec. 7, 2006.

(30) Foreign Application Priority Data

Dec. 7, 2006   (SE) ...................................... 0602634

(51) Int. Cl.
*A61B 19/00*   (2006.01)
*A61J 1/20*   (2006.01)
(Continued)

(52) U.S. Cl.
CPC . *A61J 1/2093* (2013.01); *A61J 1/10* (2013.01); *A61J 1/202* (2015.05); *A61J 1/2024* (2015.05); *A61M 1/287* (2013.01)

(58) Field of Classification Search
CPC ...................................................... A61J 1/2093
USPC ................................................. 604/403–416
See application file for complete search history.

(56) References Cited

U.S. PATENT DOCUMENTS 6,641,882 B1   11/2003   Shibata
6,645,191 B1   11/2003   Knerr et al.
(Continued)

FOREIGN PATENT DOCUMENTS

EP         0 295 204       12/1988
JP        2005-143594       6/2005
(Continued)

OTHER PUBLICATIONS

Machine translation of JP 2005-318997.*
(Continued)

*Primary Examiner* — Philip R Wiest
(74) *Attorney, Agent, or Firm* — Nixon & Vanderhye P.C.

(57) ABSTRACT

The present invention refers to a multicompartment container configured to contain a medical solution. A first compartment is defined by a first peelable seal having a first length extension, L1, and a second peelable seal having a second length extension, L2. A second compartment is defined by the first peelable seal and a third peelable seal having a third length extension, L3. A third compartment is defined by the second and the third peelable seal. The first, second, and third peelable seals are joined and L1>L2+L3. The third compartment comprises a first angle, α, between an inner side edge of the container and the third peelable seal ranging between 10°<α<80° and the first compartment comprises a second angle, β, between the first and second peelable seals ranging between 20°<β<130°.

21 Claims, 16 Drawing Sheets

(51) Int. Cl.
*A61J 1/10* (2006.01)
*A61M 1/28* (2006.01)

(56) References Cited

U.S. PATENT DOCUMENTS

| | | | |
|---|---|---|---|
| 7,935,101 B2 * | 5/2011 | Muramatsu | 604/410 |
| 2004/0134802 A1 | 7/2004 | Inoue et al. | |
| 2005/0194060 A1 | 9/2005 | Houwaert et al. | |

FOREIGN PATENT DOCUMENTS

| | | | | |
|---|---|---|---|---|
| JP | 2005-318997 | * | 11/2005 | A61J 1/00 |
| JP | 2006-043061 | | 2/2006 | |
| JP | 2011-510413 | | 3/2011 | |
| WO | WO-2007/046744 A1 | | 4/2007 | |

OTHER PUBLICATIONS

International Search Report from the Swedish Patent Office for International Application No. PCT/SE2007/001091 (Mail date Feb. 21, 2008).

* cited by examiner

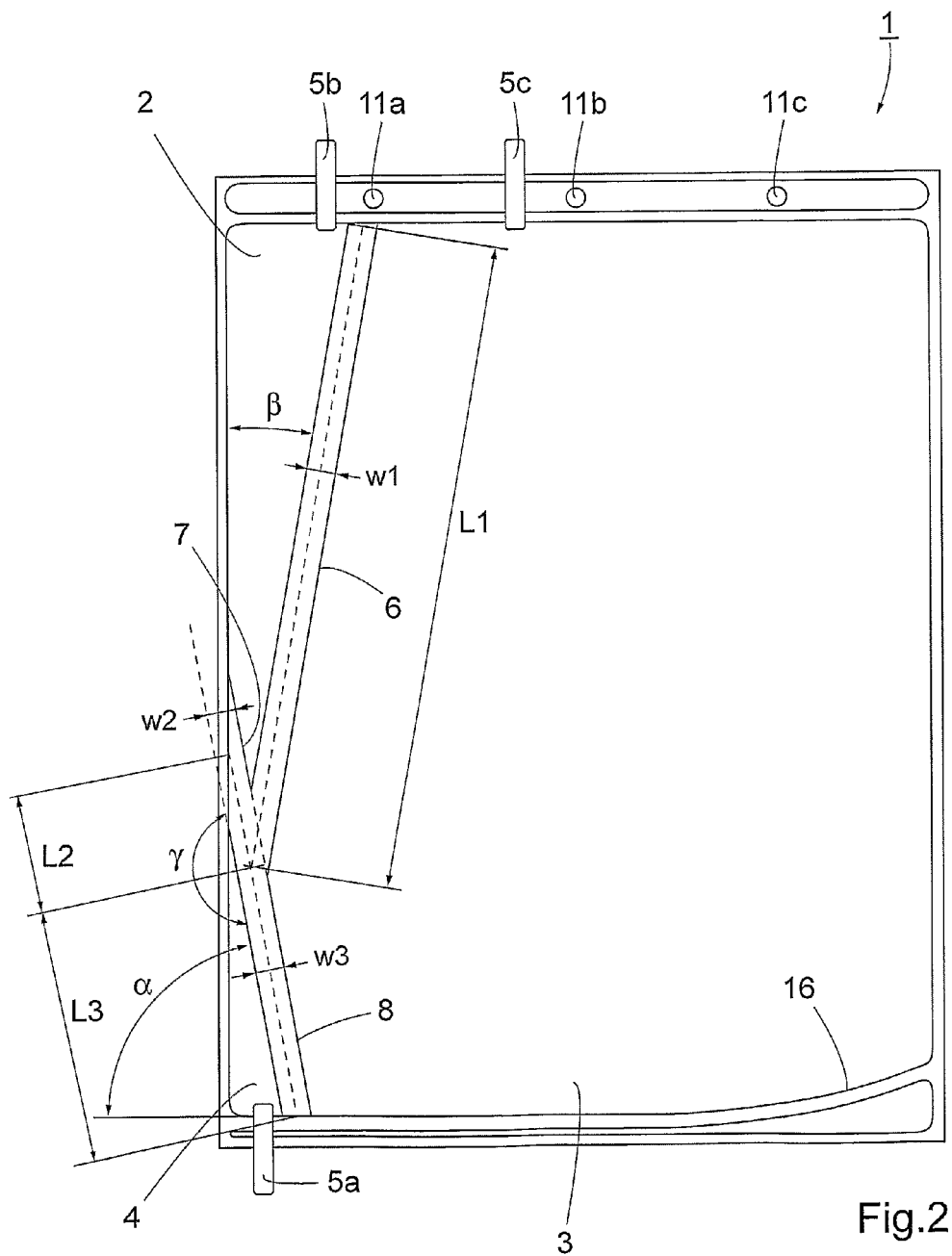

MULTICOMPARTMENT CONTAINER

CROSS REFERENCE TO RELATED APPLICATIONS

This application is a national phase application based on PCT/SE2007/001091, filed Dec. 6, 2007, and claims the priority of Swedish Patent Application No. SE 0602634-8, filed Dec. 7, 2006, and the benefit of U.S. Provisional Application No. 60/869,012, filed Dec. 7, 2006, the content of both of which is incorporated herein by reference.

TECHNICAL FIELD OF THE PRESENT INVENTION

The present invention relates to the field of multicompartment containers adapted to be filled with a medical solution. The medical solution multicompartment containers are configured for storage and mixing of at least a first single solution and a second single solution of the medical solution where the first and the second single solutions are contained in separate compartments of the container and mixed to a final medical solution before use. The compartments are separated by a peelable seal which is arranged to be ruptured by manipulation of the container for mixing of the first and the second single solution and for delivering the final medical solution through an outlet port of the multicompartment container.

BACKGROUND OF THE INVENTION

Multicompartment containers for medical solutions are frequently used. Particularly in cases where the medical solution comprises a mix of one or more single solutions which are incompatible during sterilization or storage and thus have to be kept separated. For instance a single solution that contains glucose should be kept separated from substances that catalyze the glucose degradation and also kept at a predetermined pH to further stabilize the glucose molecules. Another example is that a single solution containing bicarbonate or phosphate should be kept separated from a single solution containing calcium or magnesium in order to avoid precipitation. A further example is that a diluent and a medicament need to be maintained separated from each other. Still a further example is that a single solution with high pH needs to be maintained separated from a single solution with low pH.

The medical solution delivered to a patient should always be biocompatible. Also a medicament delivered to a patient should always be at correct concentration. For this reasons it is of great importance that the single solutions are always safely mixed before being delivered through an outlet to the patient. In case one of the above-exemplified single solutions is delivered unmixed it may be hazardous to the patient.

The need to keep single solutions of a medical solution separated in different compartments of a multicompartment container is recognized in the area of containers for administration of sterile or non-sterile medical solutions in chemical or drug therapies, for nutritional supplements, for apheresis, for parenteral administration, or for renal therapies e.g. hemodialysis, hemodiafiltration, hemofiltration or peritoneal dialysis.

An example of a flexible multicompartment solution container is known from US 2004/0134802. US 2004/0134802 discloses a medical container comprising a container body having multiple chambers for storing medicaments and a partition seal separating said chambers from each other, and an outlet attached to the container body for allowing the medicaments to be discharged from the chamber, wherein the partition seal is openable so that the chambers can communicate with each other at the time of transfer of the medical solution to a patient. The container body comprises a discharge-control seal that separates the multiple chambers from the outlet and is openable, and the force required to open the partition seal is less than that required to open the discharge-control seal.

SUMMARY OF THE INVENTION

An object of the present invention is to provide a flexible multicompartment solution container for storing and mixing a medical solution where the container comprises at least a first and a second compartment separated by a first peelable seal, where a first single solution is contained in the first compartment and a second single solution is contained in the second compartment and where the certainty is improved that the first and the second single solutions are mixed before the medical solution is ready for delivery.

Another object of the present invention is to provide a flexible multicompartment solution container where it is made substantially difficult to deliver only one of a first or a second single solution to a patient.

Such a multicompartment container is adapted for containing a medical solution which is maintained in the form of separate single solutions in separate compartments in the container until the time of transfer of the medical solution to a patient. Upon transfer the single solutions are mixed and the final medical solution is delivered through an outlet port of the multicompartment container to the patient.

The concept of "medical solution" as used in this document includes both the possibility that the solution for delivery is a concentrate that is to be diluted before delivery to the patient and the possibility that the solution for delivery is already of a suitable concentration such that it can be directly delivered to the patient. The concept "medical solution" also includes the possibility that the solution for delivery is to be mixed with other ingredients before the final medical solution to be delivered to the patient is obtained.

One example embodiment of the invention is a flexible multicompartment container that comprises the first, the second and a third compartment. The third compartment is empty or mainly empty. With mainly empty is meant that it does not contain any component of the medical solution but may optionally contain an amount of liquid sufficient for sterilizing purposes. Alternatively the third compartment is filled with a third single solution that is acceptable to deliver to a patient before being mixed with any of the first and/or the second single solutions.

The third compartment is separated from the first compartment by means of a second peelable seal and from the second compartment by means of a third peelable seal. The first, the second and the third pealable seals are joined in one point. The third compartment is provided with a port for outlet of the mixed medical solution. In an embodiment of the invention the third compartment includes one corner of the container. In an alternative embodiment of the invention the third compartment includes two corners of the container.

More specifically one example embodiment of the invention comprises a first film sheet and a second film sheet superimposed on the first film sheet forming a generally rectangular container. The film sheets are welded along their side edges providing four inner side edges. The first compartment is defined by at least one of the inner side edges and by the first peelable seal having a first length extension L1 and the second peelable seal having a second length extension L2. The second compartment is defined by at least one of the inner side edges and the first peelable seal and the third peelable seal having a third length extension L3. The third compartment is defined by at least two of the inner side edges and the second and the third peelable seals. The third compartment comprises a first angle α between one of the inner side edges and the third peelable seal, said angle α ranging between 10° and 80°, i.e. 10°≤α≤80°. The first compartment comprises a second angle β between the first and the second peelable seals, said angle β ranging between 20° and 130°, i.e. 20°≤β≤130°. However, when β is ranging between 10° and 40°, i.e. 10°≤α40°, β is ≥67×e$^{-0.03\alpha}$. The second peelable seal is arranged with an angle γ to the third peelable seal, said angle γ ranging between 160° and 200°, i.e. 160°≤γ≤200°. The length extension L1 of the first peelable seal is equal to or larger than the length extensions, L2 and L3, of the second and the third peelable seals, i.e. L1≥L2+L3. The respective length extension L2 and L3 of the second and third peelable seals is equal to or larger than 5% of the length extension of the respective second and third peelable seal, i.e. L2≥0.05 (L2+L3) and L3≥0.05(L2+L3).

According to the present invention manual manipulation of the container in such a way that pressure is exerted on the contents of either the first or the second compartment will lead to rupture of the first peelable seal and further manipulation of the mixture of the first and the second single solutions will lead to rupture of the second and the third peelable seal generally simultaneously.

Alternatively according to the invention the pressure exerted due to manual manipulation will result in that the first, the second and the third pealable seals rupture generally simultaneously.

The inventor has discovered that the length of a peelable seal is inversely proportional to its strength. This implies that a long pealable seal is weaker than a short peelable seal. Thus, the probability that the first pealable seal opens first increases the longer the first pealable seal is in comparison with the second and the third pealable seals. The design of the container provides for the pressure from the liquid to be concentrated towards the point where the first, second and third pealable seals are joined. When one or more of the pealable seals are ruptured and thus opened the opening pressure will propagate along the respective peelable seal such that each peelable seal is fully opened or opened further along its respective length extension.

More specifically; when the first compartment containing the first single solution is manipulated or a pressure is exerted on this compartment the solution will be directed towards the point where the first the second and the third pealable seals are joined. The pressure built up in the solution will exert a pressure on the first and the second pealable seals such that the first and/or the second pealable seal will open whereafter the opening pressure propagates towards the third pealable seal to open also this. At the same time the opening pressure is propagated along the first and the second pealable seal to open them further along their respective length extensions in a direction away from the point where the seals are joined.

When instead the second compartment containing the second single solution is manipulated or a pressure is exerterted upon this compartment the solution will be directed towards the point where the first, the second and the third pealable seals are joined. The pressure built up in the solution will exert a pressure on the first and the third peelable seals such that the first and/or the third peelable seal will open whereafter the opening pressure propagates toward the second peelable seal to open also this. At the same time the opening pressure is propagated along the first and the third peelable seals to open them further along their respective length extensions in a direction away from the point where the seals are joined.

In one example embodiment of the present invention the second and the third peelable seals generally have equal strength.

In one example embodiment of the present invention the first peelable seal has generally equal strength as the second and third peelable seals.

In one example embodiment of the present invention the second and the third peelable seals have an increased strength vis-à-vis the first peelable seal. The increased strength is constituted by a width of the second and the third peelable seal that is larger than the width of the first peelable seal. Alternatively, the increased strength is constituted by a longer heat sealing time or a higher heat sealing pressure than that used for the first peelable seal.

When the first, the second and the third peelable seals have been opened and the first and the second compartment are in fluid communication, mixing of the first and the second single solution takes place before outlet through the port in the third compartment.

This constitution makes it substantially difficult to deliver only one of the first and the second single solutions to a patient.

Thus the present invention provides a multicompartment container where the certainty is improved that the first and the second single solutions are mixed before the final medical solution is ready for delivery.

According to one embodiment of the invention the flexible multicompartment solution container is generally rectangular and comprises a first main sheet and a second main sheet superimposed on said first main sheet and where the medical solution container is defined at least substantially by a first, second, third and fourth edge portion, wherein the first, lower, edge portion is located opposite said second, upper, edge portion and said third, left, edge portion is located opposite said fourth, right, edge portion and where said third compartment is arranged including one corner of the container. More specifically the third compartment is defined by the second pealable seal extending from e.g. the third edge portion towards the joining point and the third pealable seal extending from the first edge portion towards the joining point, the second and the third pealable seal being joined to each other under the angle γ. The first peelable seal is arranged extending from the point where the second and the third peelable seal are joined and towards the second edge portion defining the first chamber on one side of the first peelable seal and the second chamber on the opposite side of the first peelable seal.

In one example embodiment the first edge portion has substantially the same length as the second edge portion. Similarly, according to an embodiment of the invention the third edge portion has substantially the same length as the fourth edge portion. According to an embodiment of the invention the third and fourth edge portions are longer than the first and the second end portions. According to a further embodiment of the invention the third and fourth edge portions have substantially the same length as the first and the second end portions.

In one example embodiment of the invention said first and second sheets are welded to each other along at least said first and second edge portions. To seal the first and second sheets with the help of such welds constitutes a simple manner of fabricating the solution container. It should be noted that according to a further embodiment the first and the second sheets are welded together also along the third and fourth edge portions. Alternatively it is possible that the solution container is made of a tubular material. In this case it is not necessary to seal the solution container along all of said first to fourth edge portions. If the solution container is formed from a tube, the first and second sheets are thus already connected to each other along two of said edge portions. In this case there is therefore no strict boundary between the first and the second sheets along said third and fourth edge portions, since in this case the first and second sheets actually form part of the same tubular piece.

In one example embodiment of the invention the length extension L2 of the second pealable seal is generally equal to the length extension L3 of the third peelable seal.

The term "peelable seal" refers to a low strength peelable (rupturable) seal which can be broken by the application of fluid pressure. In a solution storage container the peelable seal is preferably of a strength wherein manual squeezing of the container with liquid and/or entrapped air provides sufficient pressure to rupture and thereby open the seal.

Other objects, features, advantages and preferred embodiments of the present invention will become apparent from the following detailed description and claims when taken in conjunction with the enclosed drawings. In the following description the same number is given to the identical or similar part through the description.

BRIEF DESCRIPTION OF THE DRAWINGS

FIG. 1b is a cross-section taken along AA of FIG. 1a.

FIGS. 2-12 all schematically illustrate a plan view of alternative embodiments of a flexible medical solution multicompartment container where, like the embodiment shown in FIG. 1a, the third compartment includes one corner of the container.

DETAILED DESCRIPTION OF THE INVENTION

Figure 1A:
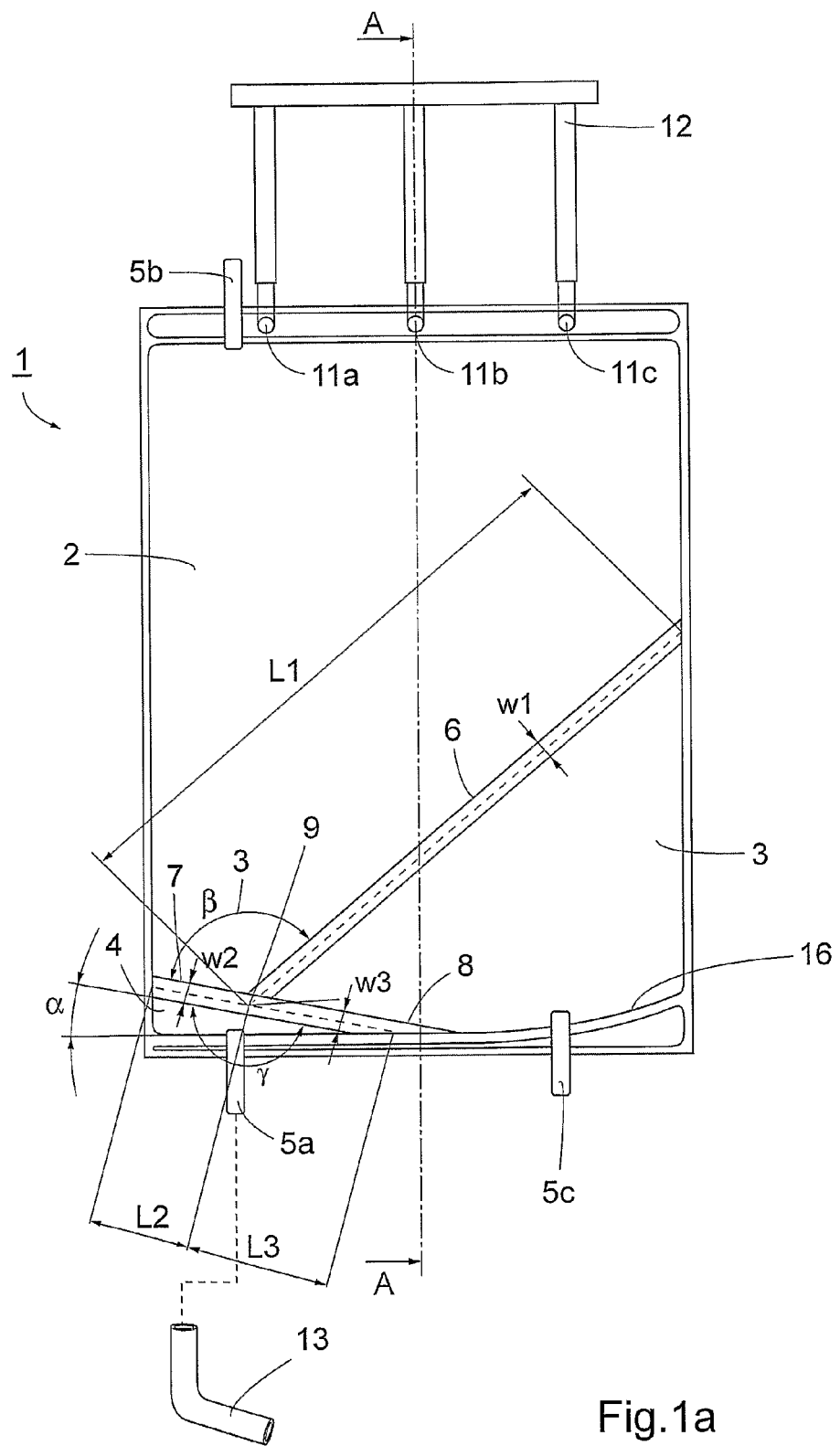
FIG. 1a schematically illustrates a plan view of an example embodiment of a flexible medical solution multicompartment container according to the present invention having a generally rectangular form.

FIG. 1a shows one example embodiment of a multicompartment container 1 for a medical solution according to the invention. The container 1 is shown as having a generally rectangular form defined by four inner side edges. The container 1 comprises a first compartment 2, a second compartment 3 and a third compartment 4. The first compartment 2 contains a first single solution and the second compartment 3 contains a second single solution. The third compartment 4 is empty or mainly empty. Alternatively the third compartment 4 is filled with a third single solution that is acceptable to be delivered directly into a patient before being mixed with any of the first and/or the second single solutions.

The first, second and third compartments 2, 3, 4 are defined by a first, a second and a third peelable seal 6, 7, 8 and at least a part of at least one of the inner side edges. More specifically the first compartment 2 is defined by a first peelable seal 6 and at least parts of three of the inner side edges of the container 1. The second compartment 3 is defined by the first peelable seal 6 and parts of two of the inner side edges of the container 1. The third compartment 4 is defined by the second and the third peelable seals 7, 8 and at least part of two of the inner side edges. The first, the second and the third pealable seals 6, 7, 8 are joined in a point 9.

The first peelable seal 6 has a first length extension L1 and the second peelable seal 7 has a second length extension L2 and the third peelable seal 8 has a third length extension L3. As illustrated in FIG. 1a the third compartment 4 is defined by the second and the third peelable seals 7, 8 and one corner of the container 1. The third compartment 4 comprises a first angle α=10° between an inner side edge of the container and the third peelable seal 8. The first compartment 2 comprises a second angle β=130° between the first 6 and the second 7 peelable seal. The second and the third peelable seals 7, 8 are arranged along a straight line, i.e. with an angle γ=180° in relation to each other.

In FIG. 1a the first length extension L1 is shown to be more or less the double length of L2+L3. The second length extension L2 is shown to be more or less equal to the third length extension L3.

The first peelable seal 6 is shown having a first width W1. The second peelable seal 7 is shown having a second width W2. The third peelable seal 8 is shown having a third width W3. In the embodiment of FIG. 1 the first, second and third widths W1, W2, W3 are shown to be more or less equal.

The upper part of the container 1 is provided with a suspension arrangement shown as holes 11a, 11b, 11c. The lower part of the container 1 has a port 5a for dispensing the medical fluid. Furtheron, the upper part of the container 1 has a port 5b for introducing the first single solution into the first compartment 3 and the lower part has a port 5c for introducing the second single solution into the second compartment 3. All ports 5a, 5b, 5c may optionally also be used for introducing supplementary agents according to an individualized prescription before delivering the final medical solution.

The lower part of the container 1 is provided with a curved weld 16. This type of curved weld is advantagous for draining the medical solution contained in the bag but is not necessary.

Figure 1B:
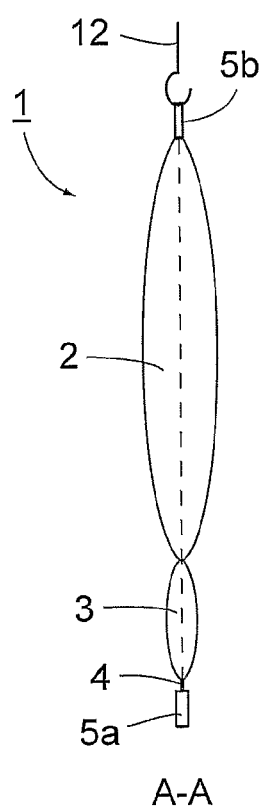
Figure 1C:
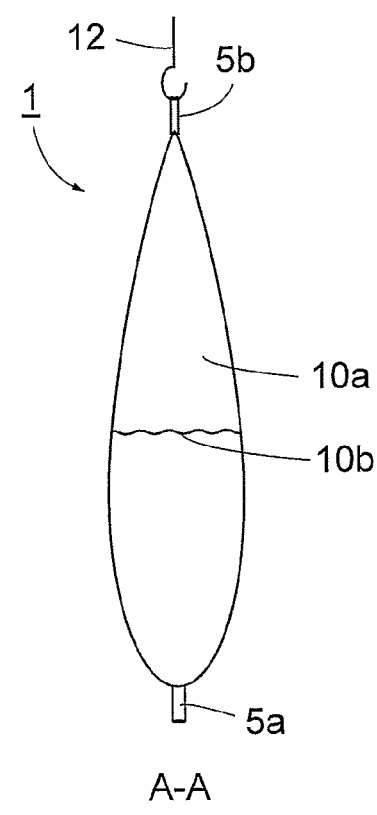
FIG. 1c is a cross-section taken along AA of FIG. 1a after the pealable seals have been ruptured.

FIG. 1b shows a cross-section taken along AA of FIG. 1a while the first, second and third peelable seals 6, 7, 8 are closed. FIG. 1c shows a cross-section taken along AA of FIG. 1a when the first, second and third peelable seals 6, 7, 8 have been ruptured and an outlet compartment 10a has been defined. Mixing of the first and the second single solutions takes place in the outlet compartment 10a. The upper level of the mixed solution is indicated by reference number 10b.

When the medical solution in the multicompartment container is to be delivered to a patient the multicompartment container according to FIG. 1a is suspended by means of the suspension arrangement in form of the holes 11a, 11b, 11c in the upper part of the container 1. The container 1 may be suspended from a suspension device 12 arranged on a bedside pole or on a machine monitoring the administration of the medical solution contained in the container 1.

Preferably before suspending the container 1 it is manipulated such that the first, the second and the third peelable seals 6, 7, 8 are ruptured fully or in part. A preferred opening procedure is to roll up the container from the upper side, i.e. the side opposite to the side including the outlet port 5a, and thereby make use of the volume of solution in either the first or the second chamber to exert a pressure large enough to rupture the first and/or the second and the third peelable seal.

An infusion tube 13 may subsequently be connected to the port 5a for outlet of the medical solution and delivery of it to a patient through the infusion tube 13. The outlet port 5a may be openable for delivery of the final medical solution by an opening means (not shown) such as a valve member, a peelable seal or a frangible pin. In case the infusion tube 13 is connected to the port before the opening of the peelable seals 6, 7, 8 no solution will be delivered. The present invention improves the certainty that only mixed medical solution is delivered through the infusion tube 13.

In the following drawings corresponding reference numbers will be used for corresponding features. Furtheron, only the differences in comparison with FIG. 1a will be described.

FIG. 2 illustrates an embodiment of the invention where the first angle α=80° and the second angle β=20°. The third length extension L3 is shown as being longer than the second length extension L2. The first length extension L1 is shown as being about twice as long as L2+L3.

Figure 3:
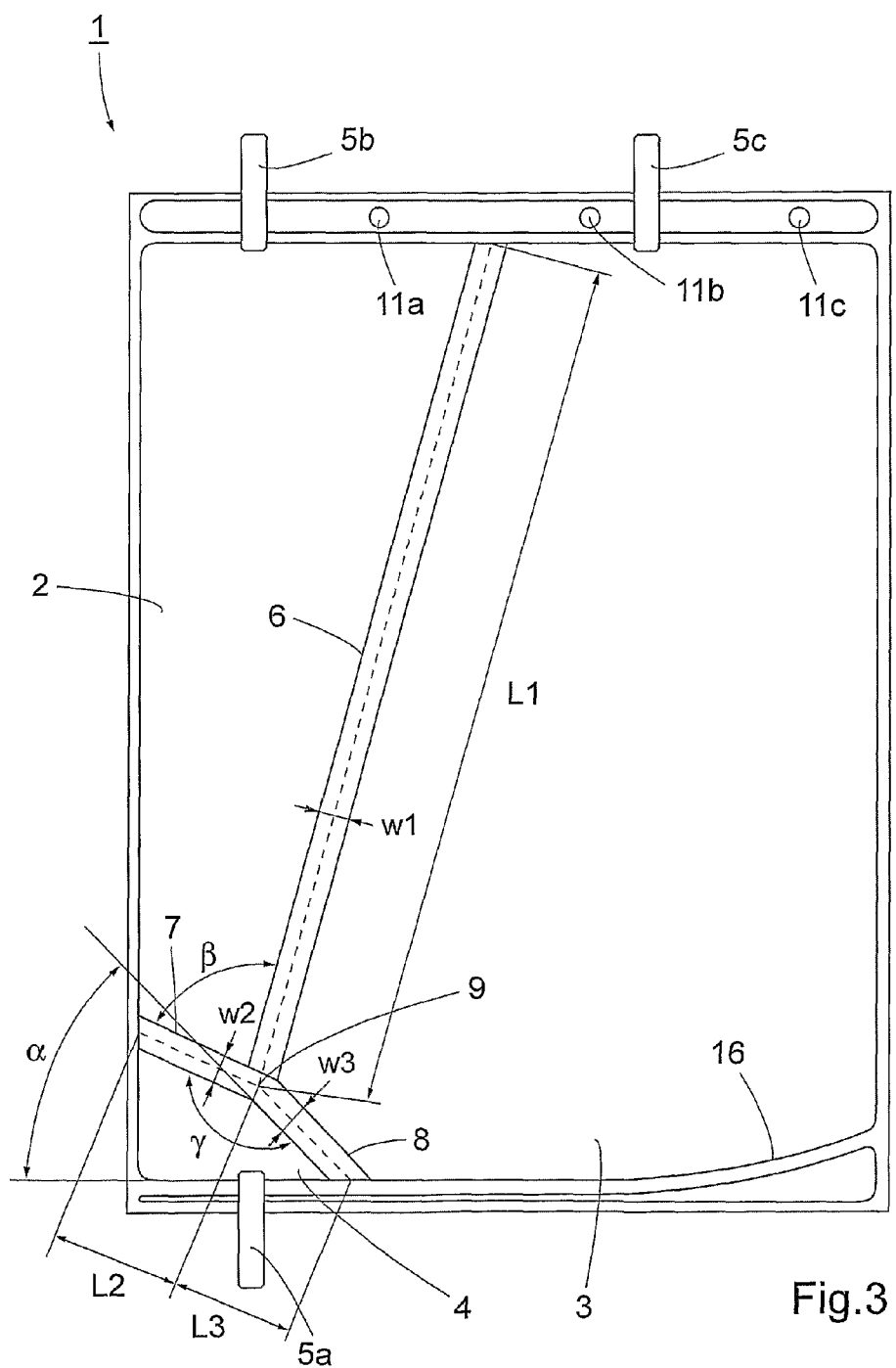

FIG. 3 illustrates an embodiment of the invention where the first angle α=45°, the second angle β=80° and the third angle γ=160°. The second and the third length extensions L2, L3 are shown as being generally equally long. The first length extension L1 is shown as being about three and a half times longer than L2+L3.

Figure 4:
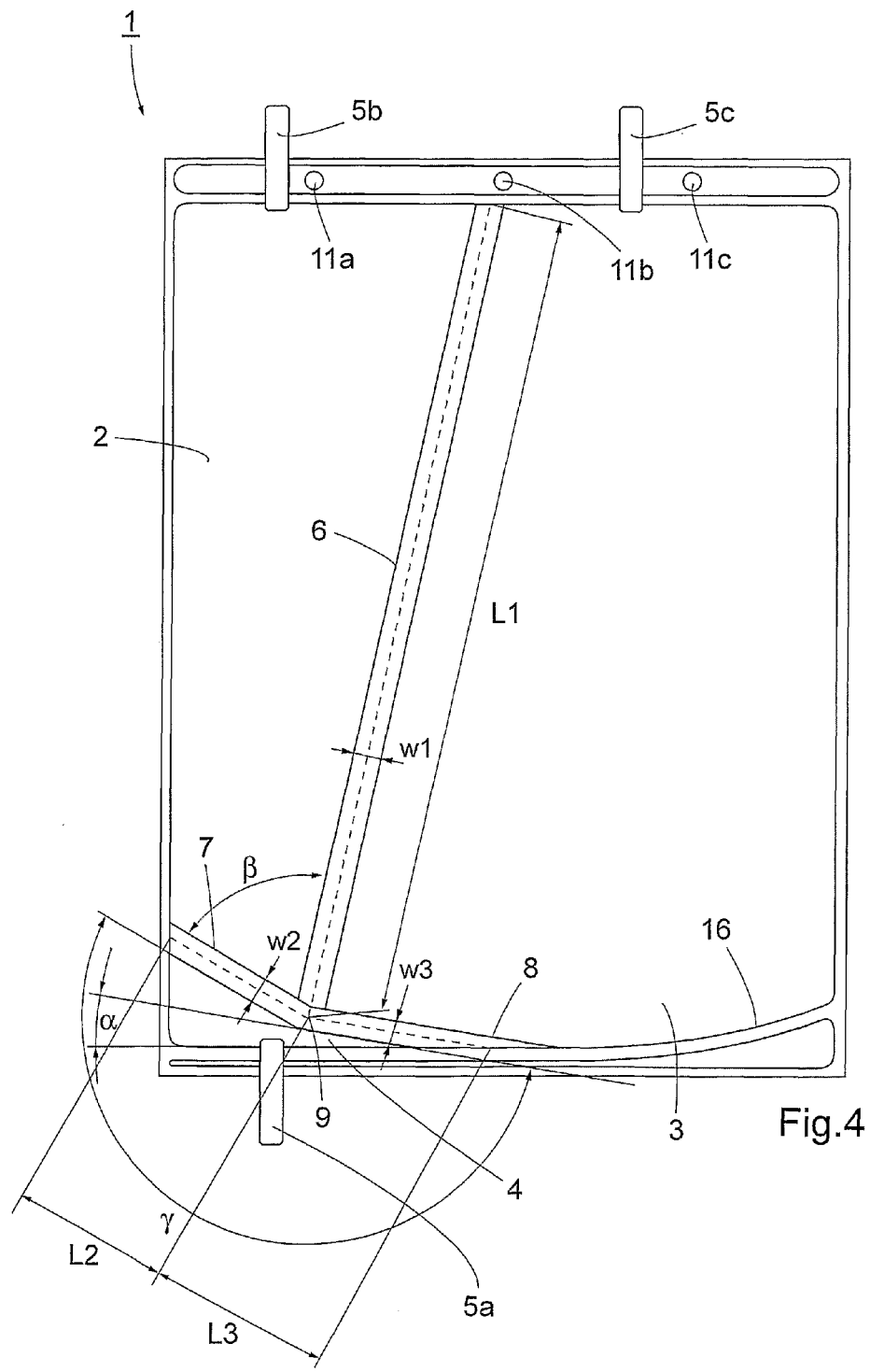

FIG. 4 illustrates an embodiment of the invention where the first angle α=10°, the second angle β=80° and the third angle γ=200°. The third length extension L3 is shown as being generally equally as long as the second length extension L2. The first length extension L1 is shown as being about two and a half times longer than L2+L3.

Figure 5:
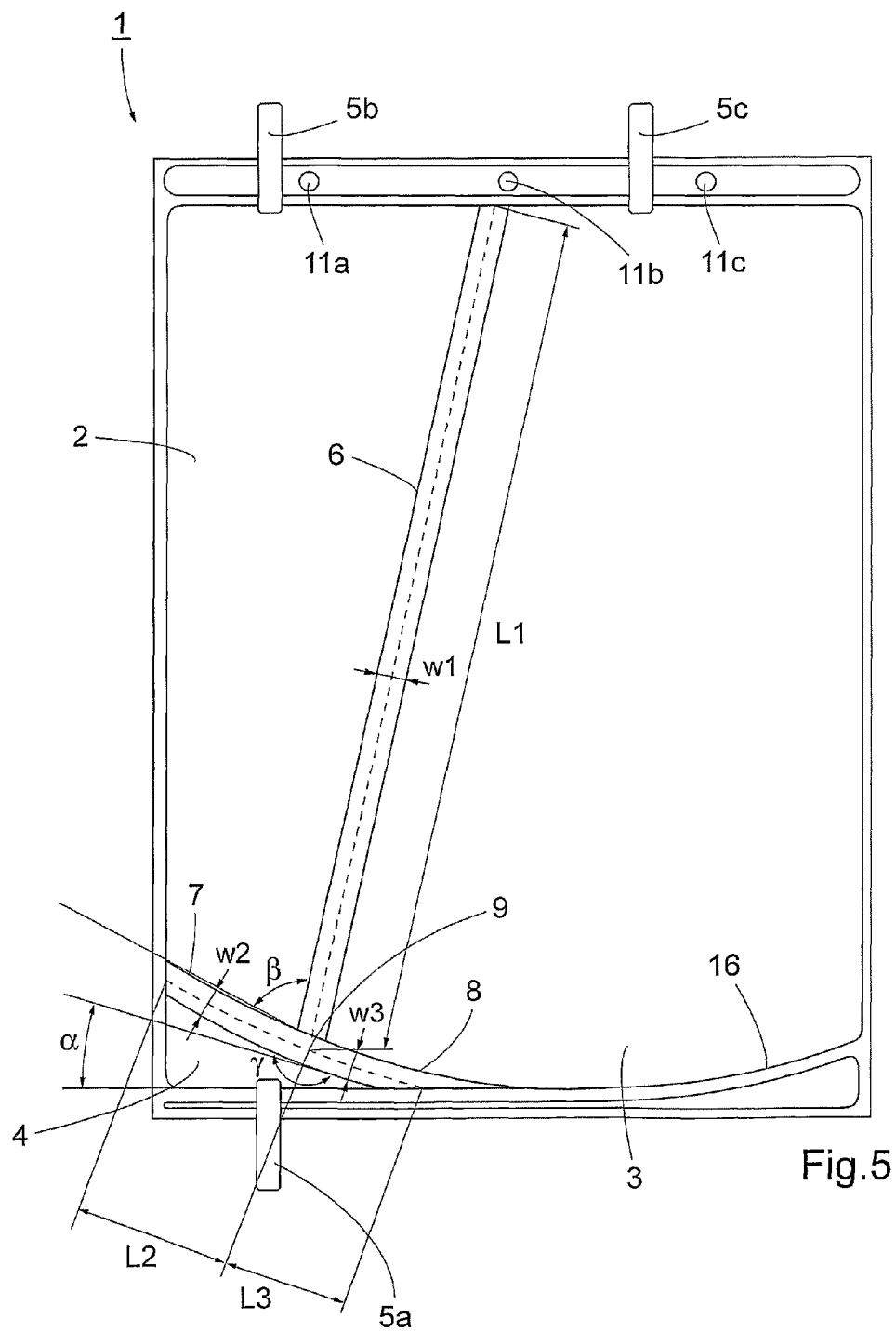

FIG. 5 illustrates an embodiment of the invention where the second and the third peelable seals 7, 8 have a curved form, shown as a U-form, where the first angle α is shown as the angle between an imaginary tangential to the curved form (the tangential starting where the third peelable seal 8 is joined with the inner side edge of the container 1) and an inner side edge of the container 1 and where the second angle β is shown as the angle between an imaginary tangential to the curved form (the tangential starting where the first and third peelable seals 6, 8 are joined) and the first peelable seal 6. The first angle α=15°, the second angle β=80° and the third angle γ=180°. The second length extension L2 is shown as being longer than the third length extension L3. The first length extension L1 is shown as being about three times longer than L2+L3.

Figure 6:
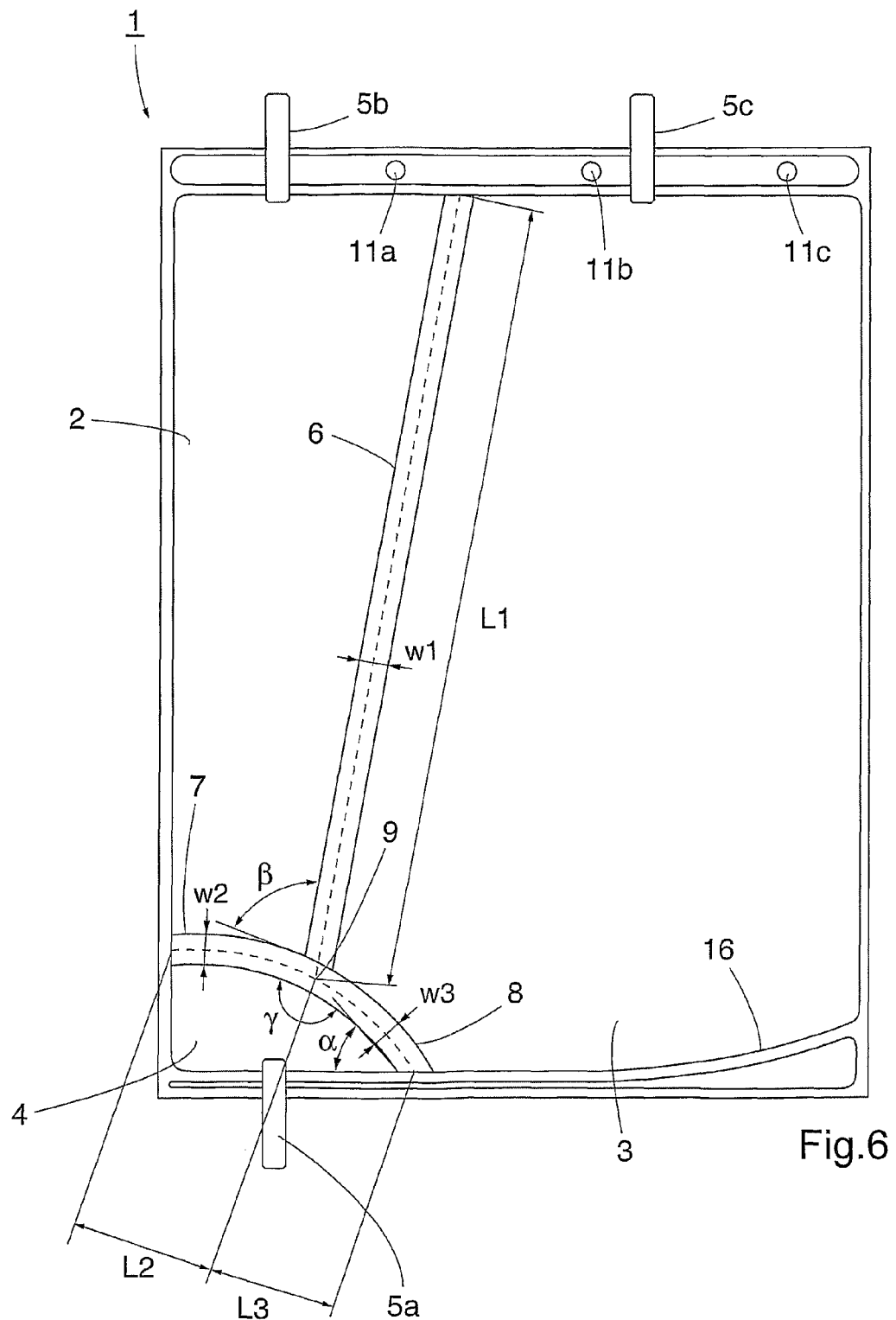

FIG. 6 illustrates an embodiment of the invention where the second and the third peelable seals 7, 8 have a curved form, shown as an inverted U-form, where the first angle α is shown as the angle between an imaginary tangential to the curved form (the tangential starting where the third peelable seal 8 is joined with the inner side edge of the container 1) and an inner side edge of the container 1 and where the second angle β is shown as the angle between an imaginary tangential to the curved form (the tangential starting where the first and third peelable seals 6, 8 are joined) and the first peelable seal 6. The first angle α=50°, the second angle β=82° and the third angle γ=180°. The second and the third length extensions L2, L3 are shown as being generally equally long. The first length extension L1 is shown as being about three times longer than L2+L3.

Figure 7:
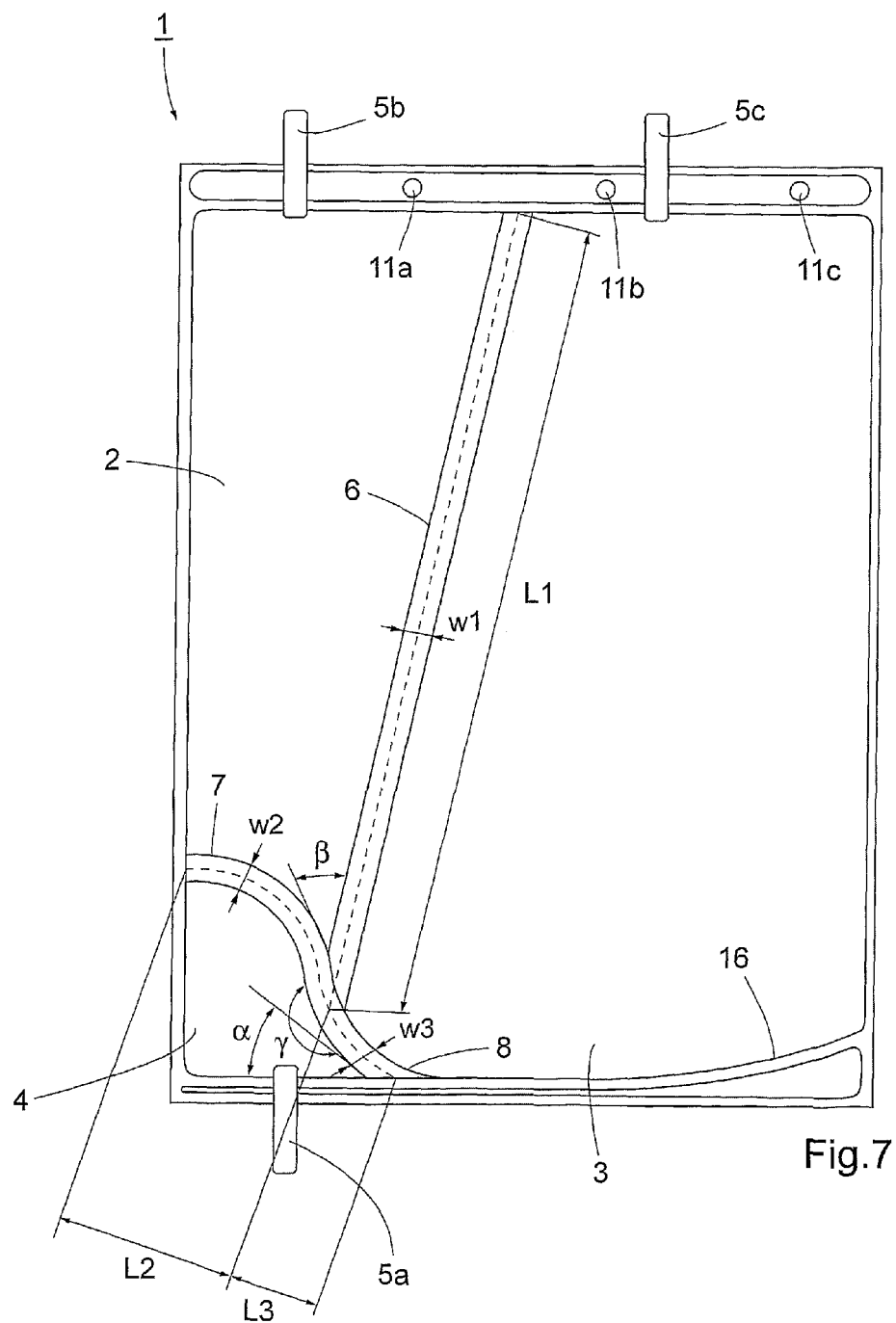

FIG. 7 illustrates an embodiment of the invention where the second and the third peelable seals 7, 8 have a curved form, shown as an inverted S-form, where the first angle α is shown as the angle between an imaginary tangential to the curved line (the tangential starting where the third peelable seal 8 is joined with the inner side edge of the container 1) and an inner side edge of the container 1 and where the second angle β is shown as the angle between an imaginary tangential to the curved form (the tangential starting where the first and third peelable seals 6, 8 are joined) and the first peelable seal 6 where the first angle α=40°, the second angle β=28° and the third angle γ=180°. The third length extension L3 is shown as being shorter than the second length extension L2. The first length extension L1 is shown as being about three times longer than L2+L3.

Figure 8:
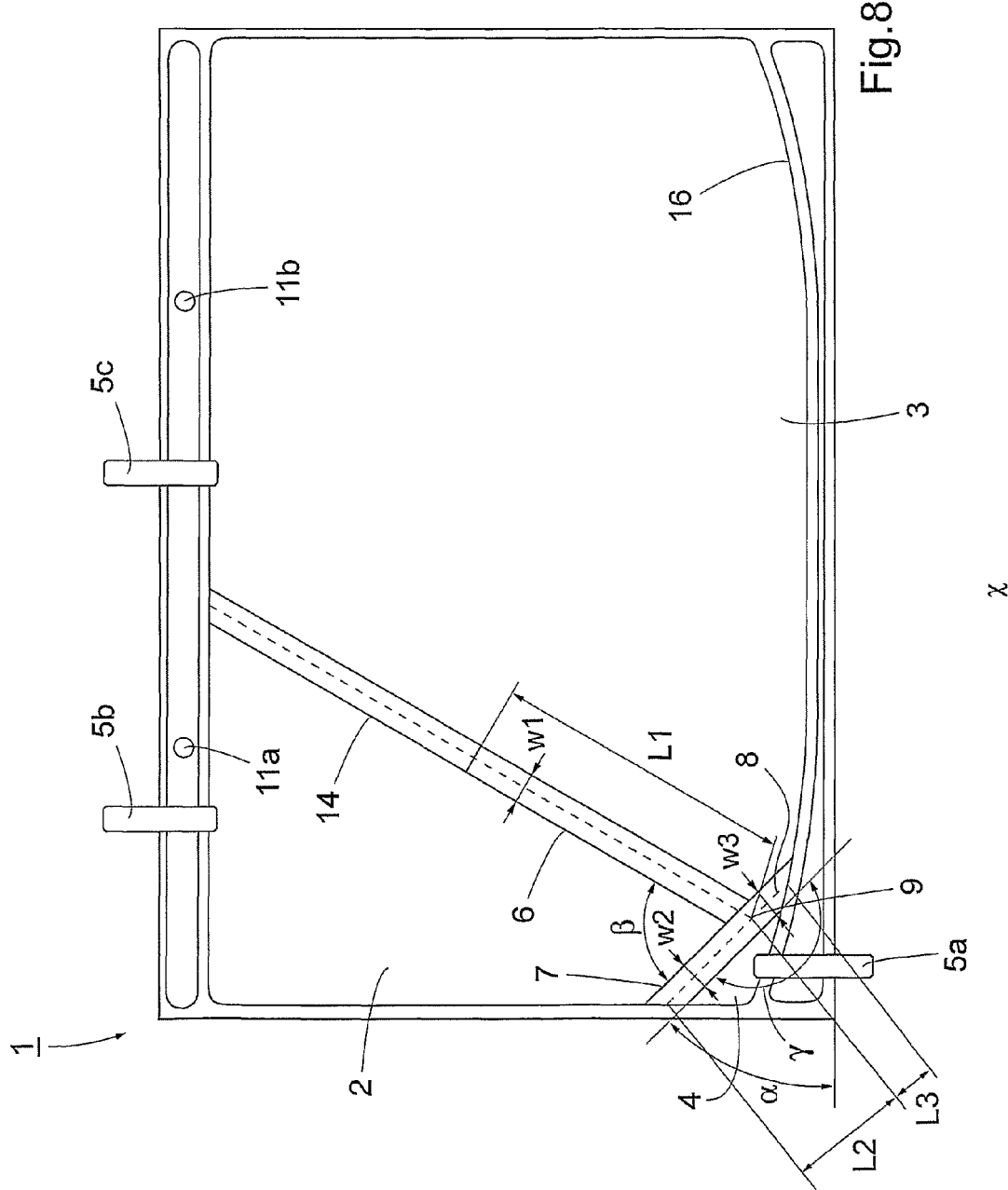

FIG. 8 illustrates an embodiment of the invention where the first angle α=45°, the second angle γ=75° and the third angle γ=180°. Further on, this embodiment comprises a permanent seal 14 which is arranged connected to and as an extension of the first peelable seal 6. The third length extension L3 is shown as being shorter than the second length extension L2. The first length extension L1 is shown as being about three times longer than L2+L3.

Figure 9:
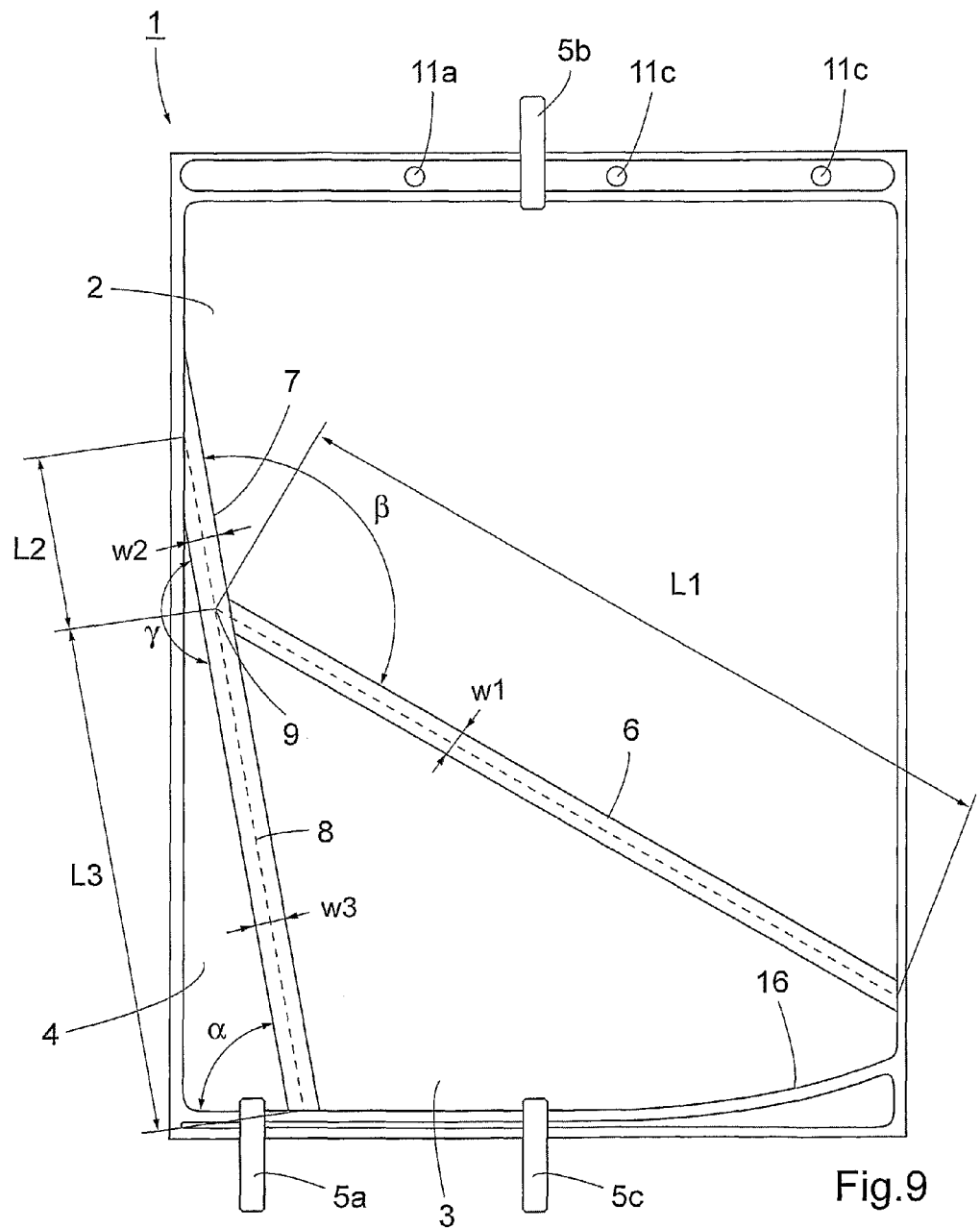

FIG. 9 illustrates an embodiment of the invention where the first angle α=80°, the second angle β=130° and the third angle γ=180°. The third length extension L3 is shown as being longer than the second length extension L2. The first length extension L1 is shown as being generally equally long as L2+L3.

Figure 10:
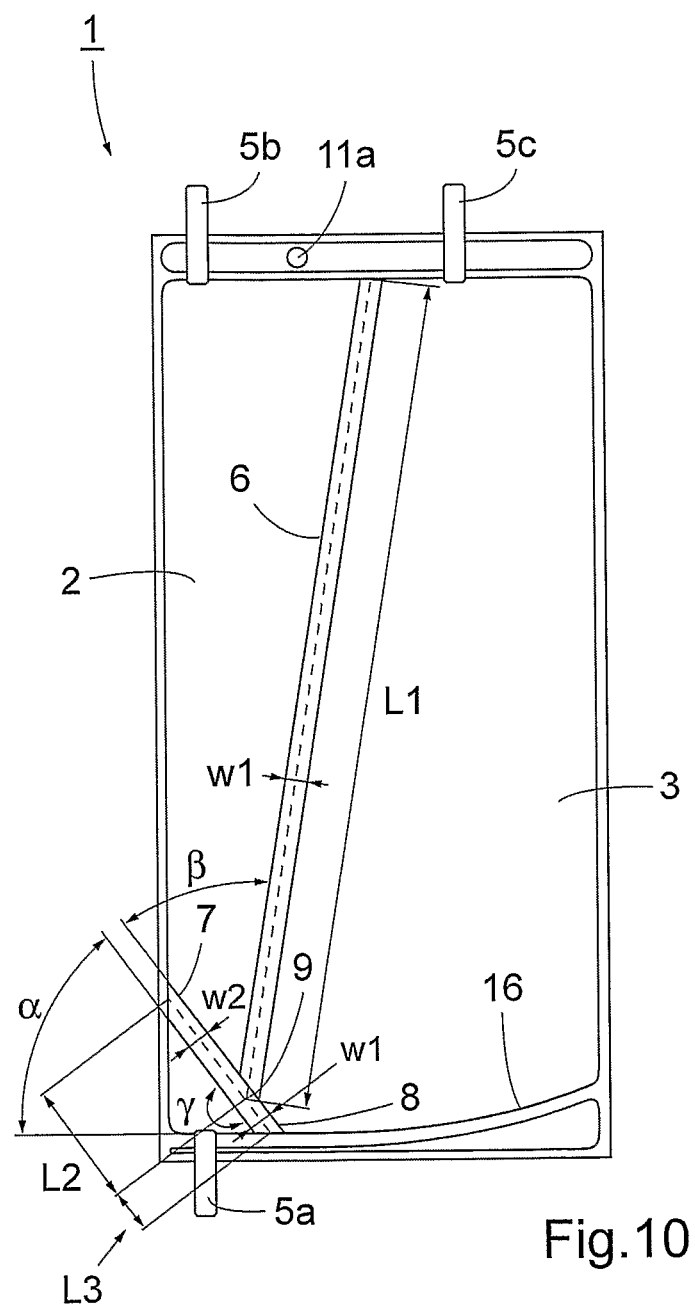

FIG. 10 illustrates an embodiment of the present invention where the first angle α=52.5° and the second angle β=46.5°. The third length extension L3 is shown as being shorter than the second length extension L2. The first length extension L1 is shown as being about five times longer than L2+L3.

Figure 11:
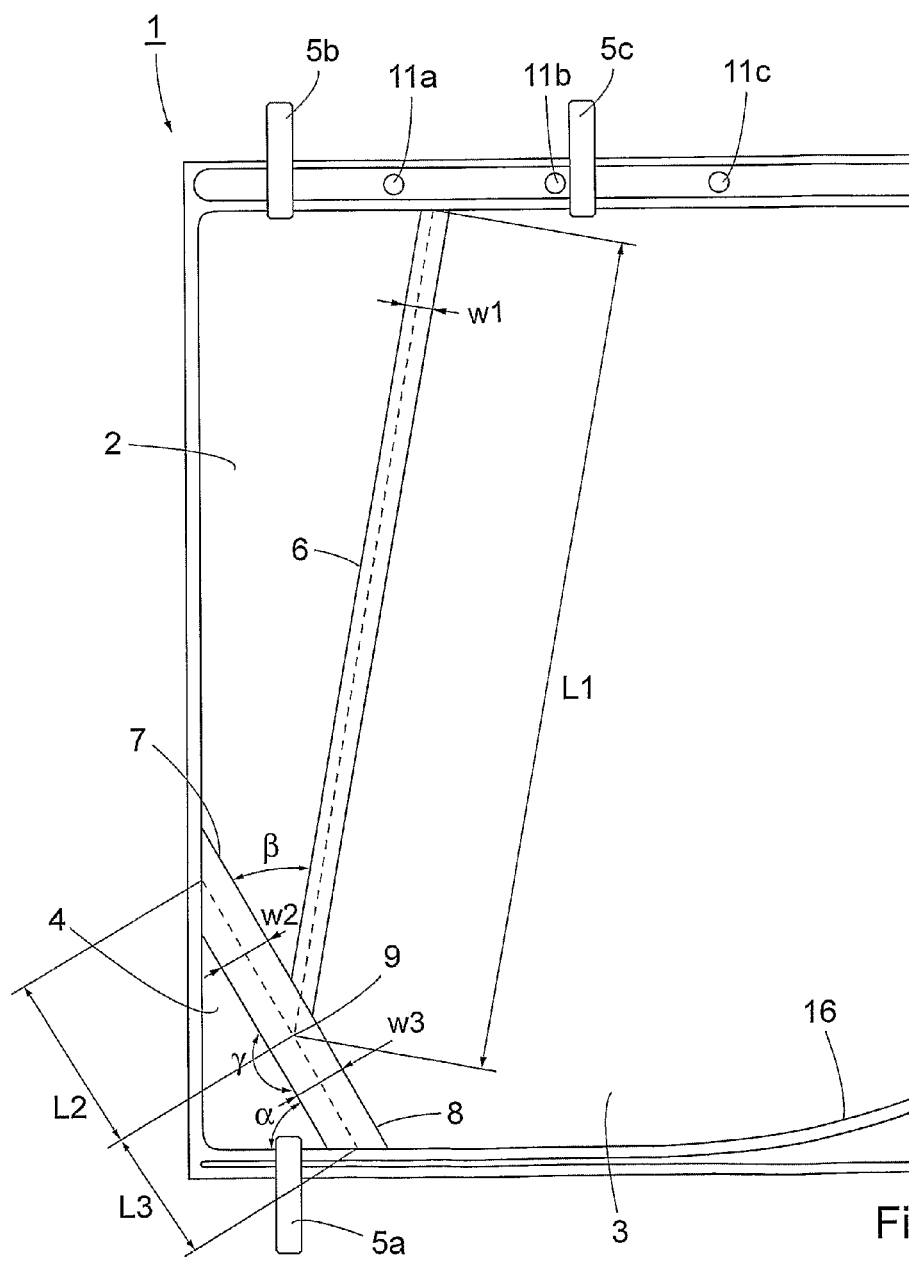

FIG. 11 illustrates a preferred embodiment of the present invention. In this embodiment the first angle α=60° and the second angle β=40°. The second 7 and the third 8 peelable seals are arranged along a straight line, i.e. with an angle γ=180°. The second 7 and the third 8 peelable seals are provided with widths W2, W3 which generally are twice as wide as the width W1 of the first peelable seal 6. Widths W2, W3 of the second and third peelable seals 7, 8 that are larger than the width W1 of the first peelable seal 6 implies stronger second and third peelable seals 7, 8. Thus the propensity that the first peelable seal 6 is opened before the second and the third peelable seals 7, 8 is increased. The third length extension L3 is shown as being generally equally as long as the second length extension L2. The first length extension L1 is shown as being about three times longer than L2+L3.

Figure 12:
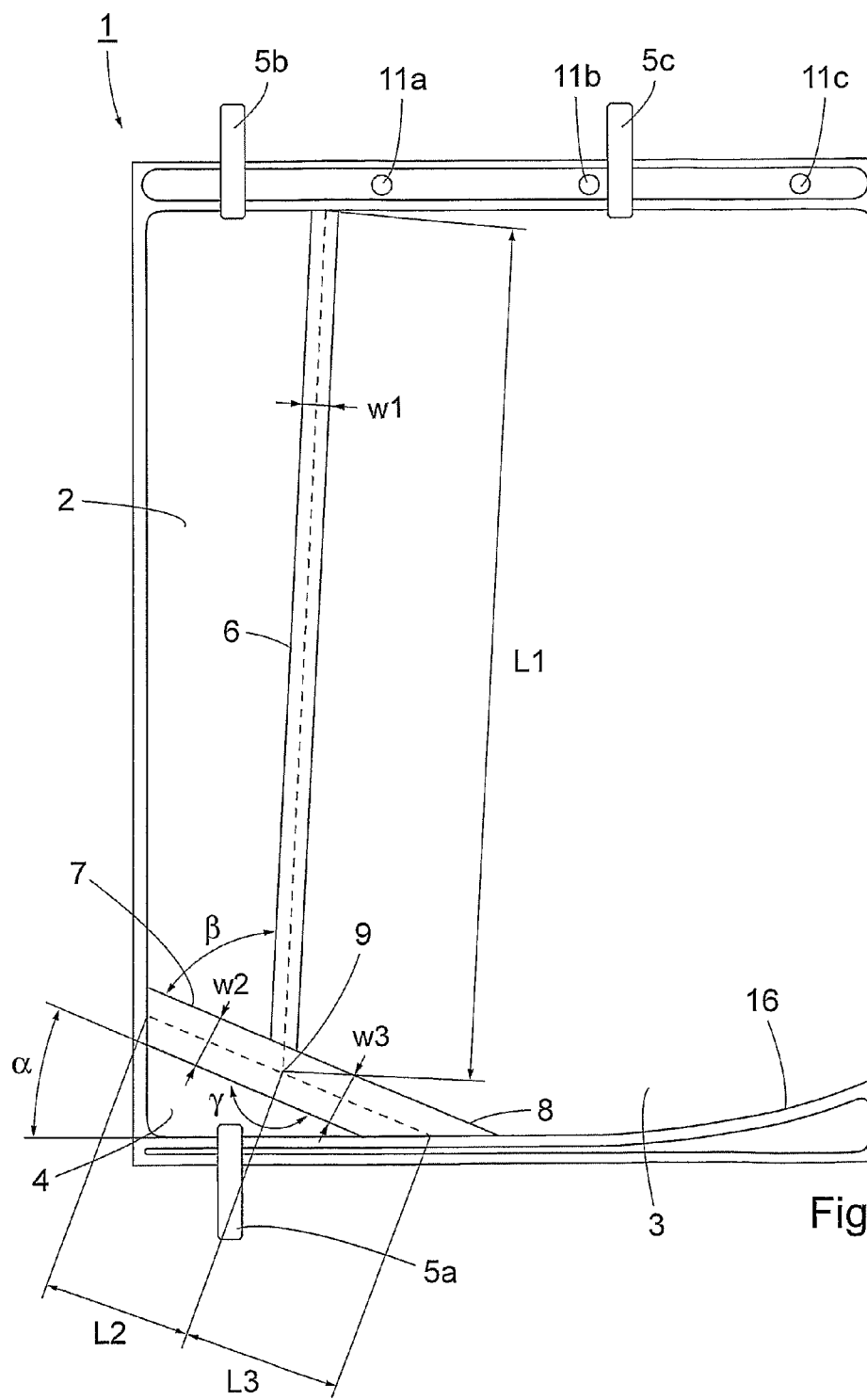

FIG. 12 also illustrates a preferred embodiment of the present invention. In this embodiment the first angle α=23° and the second angle β=70°. The rest of the features correspond to the features described in connection with FIG. 11.

Figure 13:
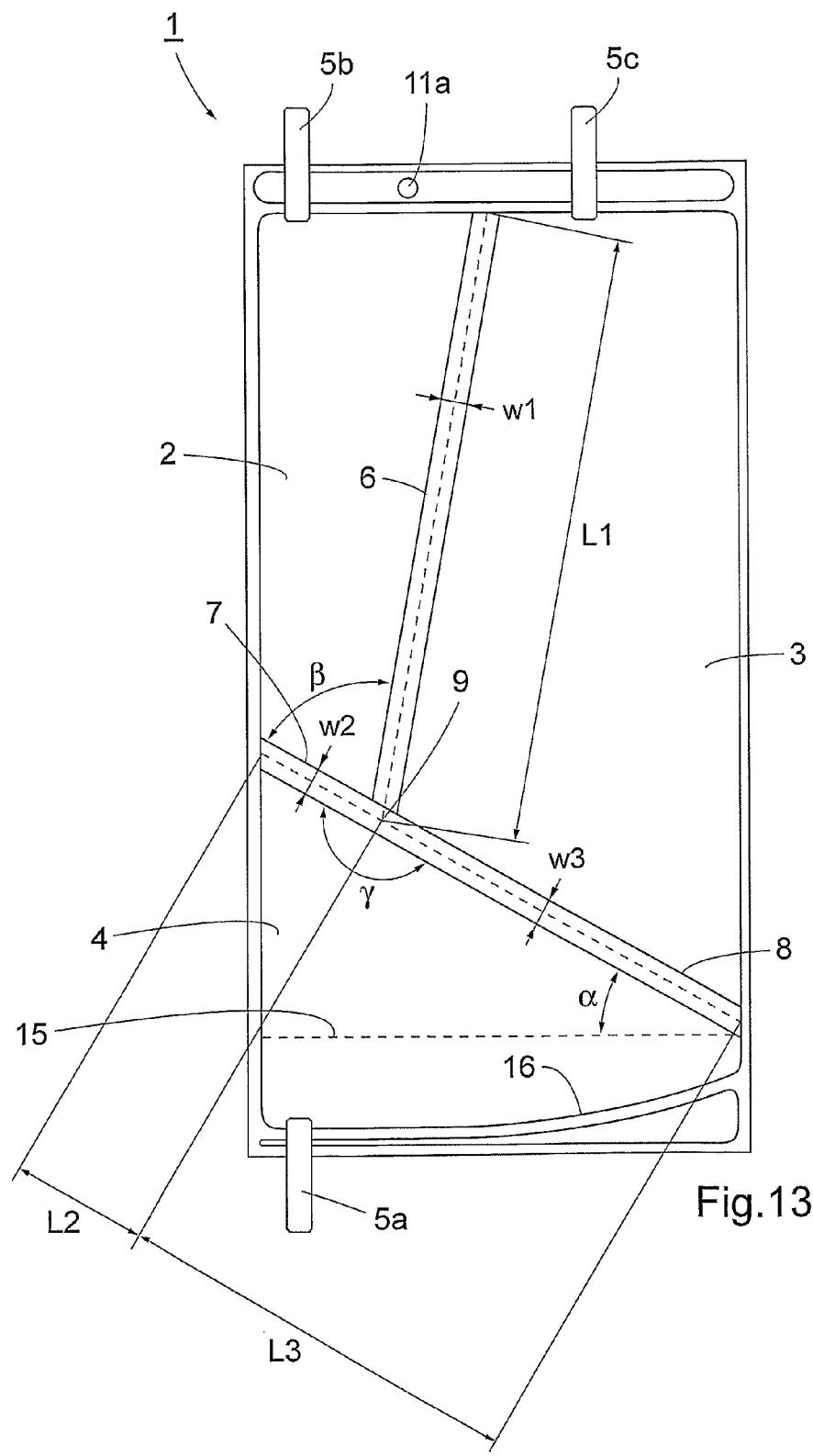
FIG. 13 schematically illustrates a plan view of a further alternative embodiment of a flexible medical solution multicompartment container where the third compartment includes two corners of the container.

FIG. 13 illustrates an embodiment of the invention where the first angle α is defined between an imaginary line 15 that is parallel to the inner(lower) side edge of the container and the third peelable seal 8. In this embodiment α=30°, β=70° and γ=180°. The third length extension L3 is shown as being longer than the second length extension L2. The first length extension L1 is shown as being generally equally as long as L2+L3.

Figure 14:
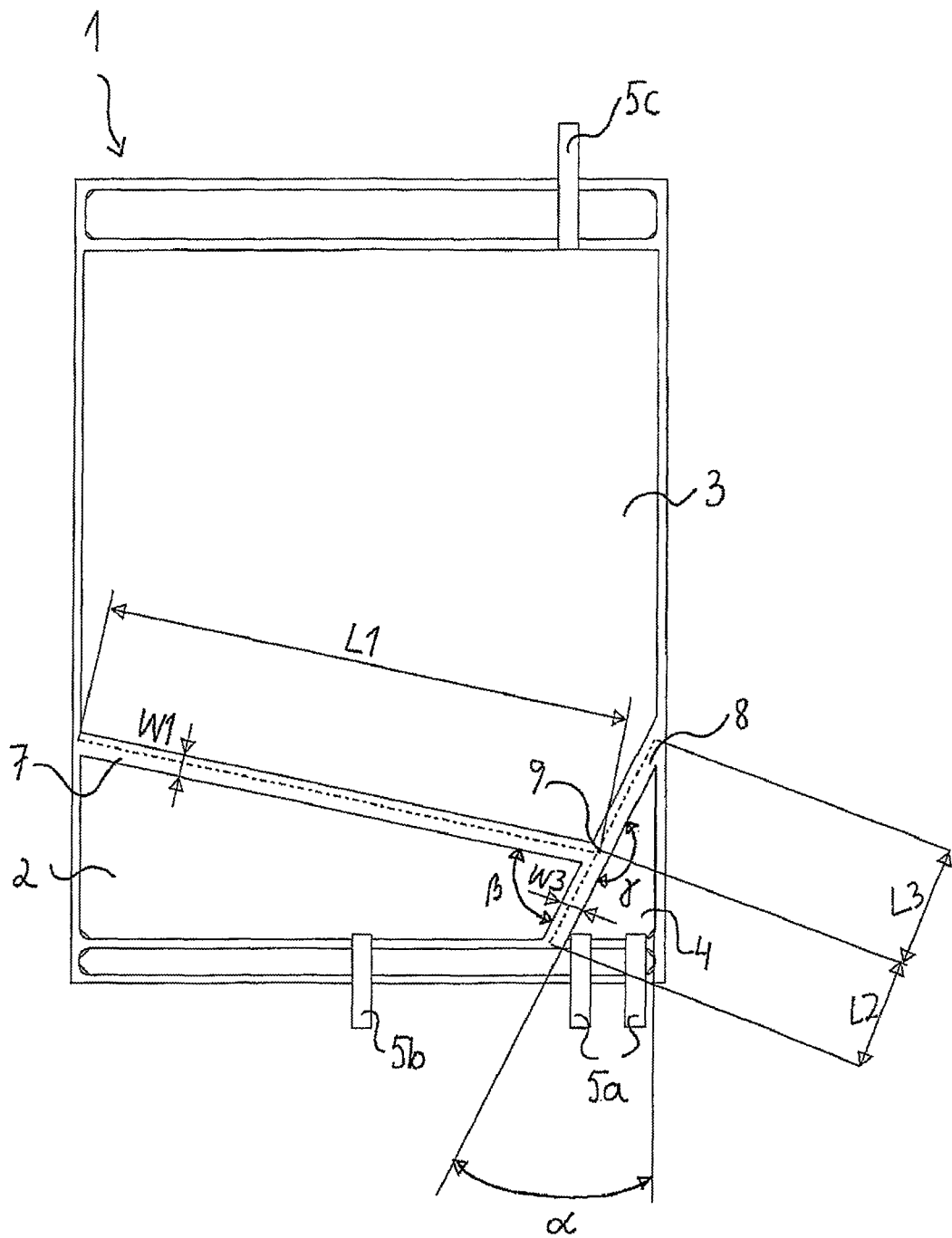
FIGS. 14 and 15 schematically illustrates a plan view of alternative embodiments of a flexible medical solution multicompartment container where the lower part is provided with two outlet ports for allowing alternative connectability in one and the same container.

FIG. 14 illustrates an embodiment of the invention where the first angle α=27° and the second angle β=75°. In this embodiment the lower part of the container 1 is provided with two outlet ports 5a for dispensing the medical fluid. By having two outlet ports 5a arranged in the third compartment 4, alternative connectability may be provided in one and the same container 1. More specifically two different types of connectors may be provided. One of the outlet ports 5a may for example be provided with a connector of Luer type and one of the outlet ports 5a may be provided with a connector comprising a frangible pin. The connectors as such are not shown in the drawing. The rest of the features shown in FIG. 14 correspond to the features described in connection with FIG. 1a.

Figure 15:
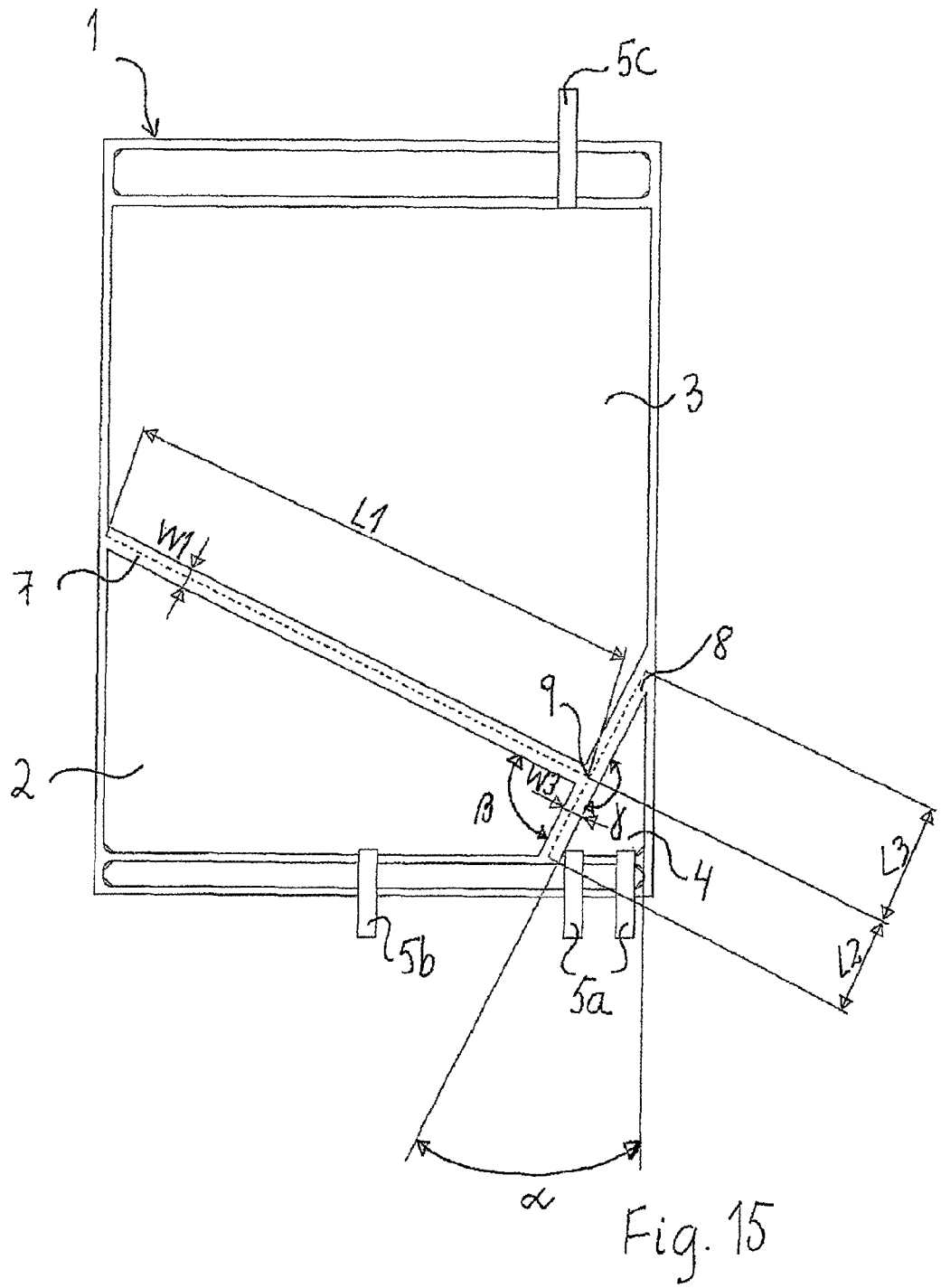

FIG. 15 illustrates an embodiment of the invention where the first angle α=27° and the second angle β=89°. The rest of the features shown in FIG. 15 correspond to the features described in connection with FIG. 14. The multicompartment container 1 is adapted for containing a wide range of medical fluids such as medical fluids for nutrition or for use in hemodialysis treatments, chronic as well as acute, and peritoneal dialysis treatments.

A multicompartment container according to the present invention would typically be configured sufficiently large for containing 0.3 to 10 liters of medical solution. Large volumes of medical solution are especially of interest when performing longlasting treatments, e.g. nightly treatments such as continuous peritoneal dialysis or in connection with intensive care.

In one example embodiment of the invention the multicompartment container 1 shown in FIG. 11 contains a total volume of 2 liters of medical solution. The first compartment 2 contains 100-400 ml of a first single solution and the second compartment 3 contains 1600-1900 ml of a second single solution.

In one example embodiment of the invention the multicompartment container 1 shown in FIG. 12 contains a total volume of 5 liters of medical solution. The first compartment 2 contains 4000-4800 ml of a first single solution and the second compartment 3 contains 200-1000 ml of a second single solution.

In one example embodiment of the present invention the third compartment 3 is containing water or saline for sterilization purposes. By containing water or saline in the third compartment sterility of the multicompartment container may be assured at a lower temperature, i.e. at about 120 degrees Celcius instead of at about 185 degrees Celcius.

The present invention has above been disclosed as containing a medical solution in the first and second compartment respectively. In an alternative embodiment the first compartment 2 instead comprises a medical component in powder or granular form to be dissolved by means of a solution, e.g. the medical solution in the second compartment 3. In case the medical solution in the second compartment 3 is to be used to dissolve the medical component in powder form the first and/or the third peelable seal 6, 8 is/are ruptured by manipulating the solution in the second compartment 3 to exert pressure on and rupturing the peelable seals 6, 8 and subsequently the second peelable seal 7.

In one example embodiment of the present invention the multicompartment container is made from a plastic peelable film e.g. a non-PVC film.

In case a film material of the multicompartment container 1 is chosen that does not have a high enough oxygen barrier the multicompartment container 1 may be enclosed in an overwrap (not shown) with high enough oxygen barrier in the film material.

The medical solution is of such a concentration that the solution is suitable to be delivered through the outlet port 5a to a patient without being further diluted. Alternatively the medical solution is in a concentrated form such that the solution is to be diluted before being delivered through the outlet port 5a to a patient.

In an example embodiment of the present invention a fourth peelable seal (not shown) is arranged in the third compartment 4 between the second and the third peelable seal 7, 8 and the outlet port 5a.

Above has been disclosed a multicompartment container 1 which generally is rectangular or square and provided with four side edges or corners. However, the present invention is applicable also in containers having e.g. three or five or more side edges or corners.

The invention is not limited to the described embodiments but may be varied and modified within the scope of the following claims.

The invention claimed is:

1. A flexible multicompartment container configured to contain a medical solution, comprising
   a first film sheet;
   a second film sheet superimposed on and connected to the first film sheet forming multiple inner side edges;
   a first compartment defined by at least a part of at least one of the multiple inner side edges and a first peelable seal having a first length extension (L1) and a second peelable seal having a second length extension (L2);
   a second compartment defined by at least a part of at least one of the multiple inner side edges, the first peelable seal, and a third peelable seal having a third length extension (L3);
   a third compartment defined by at least a part of at least two of the multiple inner side edges, the second, and the third peelable seal;
   the first, the second, and the third peelable seals being joined, and wherein
   a first angle ($\alpha$) extends through the third compartment, is between one of the inner side edges and the third peelable seal, and is in a range of ten degrees (10°) to eighty degrees (80°);
   a second angle ($\beta$) extends through the first compartment, is between the first and the second peelable seal, and is in a range of twenty degrees (20°) to one-hundred thirty degrees (130°);
   a third angle ($\gamma$) extends through the third compartment, is between the second peelable seal and the third peelable seal, and in a range of one-hundred sixty degrees (160°) to two-hundred degrees (200°), wherein:

$$L1 > L2 + L3;$$

$$L2 > 0.05(L2 + L3);\text{ and}$$

$$L3 > 0.05(L2 + L3).$$

2. A multicompartment container according to claim 1, wherein $\gamma = 180°$.

3. A multicompartment container according to claim 1 or 2, wherein $40° \leq \alpha \leq 80°$ and $30° \leq \beta \leq 130°$.

4. A multicompartment container according to claim 1 or 2, wherein $50° \leq \alpha \leq 70°$ and $40° \leq \beta \leq 60°$.

5. A multicompartment container according to claim 2, wherein $\alpha = 60°$ and $\beta = 40°$.

6. A multicompartment container according to claim 2, wherein $\alpha = 23°$ and $\beta = 70°$.

7. A multicompartment container according to claim 2, wherein $\alpha = 27°$ and $\beta = 75°$.

8. A multicompartment container according to claim 2, wherein $\alpha = 27°$ and $\beta = 89°$.

9. A multicompartment container according to claim 1, wherein L1 = 3(L2+L3).

10. A multicompartment container according to claim 1, wherein the second length extension (L2) is substantially equal to the third length extension (L3).

11. A multicompartment container according to claim 1, wherein the first, second, and third peelable seals have substantially equal strength.

12. A multicompartment container according to claim 1, wherein the second and third peelable seals have an increased strength in comparison with the strength of the first peelable seal.

13. A multicompartment container according to claim 12, wherein the increased strength is constituted by the width (W2) of the second peelable seal and the width (W3) of the third peelable seal, said widths (W2, W3) being larger than the width (W1) of the first peelable seal.

14. A multicompartment container according to claim 12, wherein the increased strength is further constituted by a longer heat sealing time or a higher heat sealing pressure than that used for the first peelable seal.

15. A multicompartment container according to claim 1, wherein the third compartment comprises at least one outlet port.

16. A multicompartment container according to claim 1, wherein the multicompartment container is configured to contain 300 ml to 10 liters of medical solution.

17. A multicompartment container according to claim 16, wherein the first compartment is configured to contain 100-400 ml of a first single solution and the second compartment is configured to contain 1600-1900 ml of a second single solution.

18. A multicompartment container according to claim 16, wherein the first compartment is configured to contain 200-1000 ml of a first single solution and the second compartment is configured to contain 4000-4800 ml of a second single solution.

19. A flexible multicompartment container configured to contain a medical solution comprising:
   a first film sheet superimposed with a second film sheet and sealed together along edges of the superimposed films, wherein a compartment area is defined by interior edges of the sheets when sealed together, and the compartment area includes a first peelable seal having a first length (L1), a second peelable seal having a second length (L2) and a third peelable seal having a third length (L3);
   a first medical solution compartment between the first and second film sheets, within the compartment area, and having an edge adjacent the first peelable seal and the second peelable seal;
   a second medical solution compartment between the first and second film sheets, within the compartment area, and separated from the first medical solution compartment by the first peelable seal and having an edge adjacent the third peelable seal;
   a third compartment between the sheets, within the compartment area and adjacent the second peelable seal and third peelable seal;
   wherein the first, the second, and the third peelable seals intersect;
   the third compartment forms a first angle ($\alpha$) between one of the inner edges and the third peelable seal and the first angle is in a range of ten degrees (10°) to eighty degrees (80°);
   the first compartment forms a second angle ($\beta$) between the first peelable seal and the second peelable seal and the second angle is in a range of twenty degrees (20°) to one-hundred and thirty degrees (130°), and
   the second peelable seal forms a third angle ($\gamma$) with respect to the third peelable seal and the third angle is in a range of one-hundred and sixty degrees (160°) and two-hundred degrees (200°), and L1 is at least as long as the sum of L2 and L3.

20. The flexible multicompartment container of claim 1 the first angle ($\alpha$) is in a range of $10° \leq \alpha \leq 40°$, and $\beta$ is $\geq 67e^{-0.03\alpha}$.

21. A flexible multicompartment medical solution container comprising:
   opposing and overlapping film sheets sealed together along a perimeter of the sheets;
   first, second and third compartments between the film sheets, wherein each compartment is adjacent and within the perimeter;
   a first peelable seal joining the sheets and separating the first and second compartments;
   a second peelable seal joining the sheets and separating the first and third compartments, and
   a third peelable seal joining the sheets and separating the second and third compartments, wherein:
   an alpha ($\alpha$) angle is between the second peelable seal and the perimeter, has an apex at a corner of the third compartment and is in a range of 10 to 80 degrees;
   a beta ($\beta$) angle is between the first and second peelable seals, has an apex at a corner of the first compartment and is in a range of 20 to 130 degrees, and
   a gamma ($\gamma$) angle is between the second and third peelable seals, has an apex at a corner of the third compartment and is in a range of 160 to 200 degrees,
   wherein the length of the first peelable seal is at least as long as the sum of the lengths of the second and third peelable seals.

\* \* \* \* \*